(12) United States Patent
Hafer et al.

(10) Patent No.: US 6,456,874 B1
(45) Date of Patent: *Sep. 24, 2002

(54) INSTRUMENT FOR DELIVERY OF ANAESTHETIC DRUG

(75) Inventors: Fred Hafer, Shillington, PA (US); Michal Syrucek, Hradec Kralove (CZ); Andre Boezaart, Pearl (ZA)

(73) Assignee: Arrow International Inc., Reading, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/524,467

(22) Filed: Mar. 13, 2000

(51) Int. Cl.[7] ................................. A61N 1/30
(52) U.S. Cl. ....................................... 604/21
(58) Field of Search ................ 607/3, 116, 117, 607/120, 127; 604/21; 600/554

(56) References Cited

U.S. PATENT DOCUMENTS

| | | | |
|---|---|---|---|
| 4,518,383 A | | 5/1985 | Evans |
| 4,644,960 A | | 2/1987 | Johans |
| 4,824,433 A | * | 4/1989 | Marz et al. .................. 604/21 |
| 5,007,902 A | * | 4/1991 | Witt ........................... 600/554 |
| 5,135,525 A | | 8/1992 | Biscoping et al. |
| 5,304,141 A | | 4/1994 | Johnson et al. |
| 5,423,877 A | | 6/1995 | Mackey |
| 5,830,151 A | * | 11/1998 | Hadzic et al. .............. 600/554 |
| 5,976,110 A | | 11/1999 | Greengrass et al. |
| 6,298,256 B1 | | 10/2001 | Meyer |

FOREIGN PATENT DOCUMENTS

WO    WO 99/04705 A1    4/1999

* cited by examiner

Primary Examiner—William E. Kamm
Assistant Examiner—Jeffrey P. Jastrzab
(74) Attorney, Agent, or Firm—Amster, Rothstein & Ebenstein

(57) ABSTRACT

A needle and catheter system, including components, is provided such that the position of an epidural needle may be identified after insertion into the body of a patient by electrically stimulating and thus locating a specific nerve. When a specific nerve is located, the catheter is inserted through the needle to a point slightly beyond the distal tip of the needle. The catheter tip may then be manipulated and the optimum position for the catheter tip determined by applying an electrical voltage through the helical wire to the proximal tip of the helical wire, this electrical stimulation being utilized in locating the specific location of the catheter tip within the nerve. Once optimum placement is achieved, the catheter is utilized for continuous administration of anaesthetic. A catheter adapter is utilized to allow easy access to the catheter and introduction of fluid into the nerve of the patient through the catheter tip. The catheter and catheter adapter are also provided with components so that the catheter adapter can be in place for during electrical stimulation of the target nerve.

1 Claim, 5 Drawing Sheets

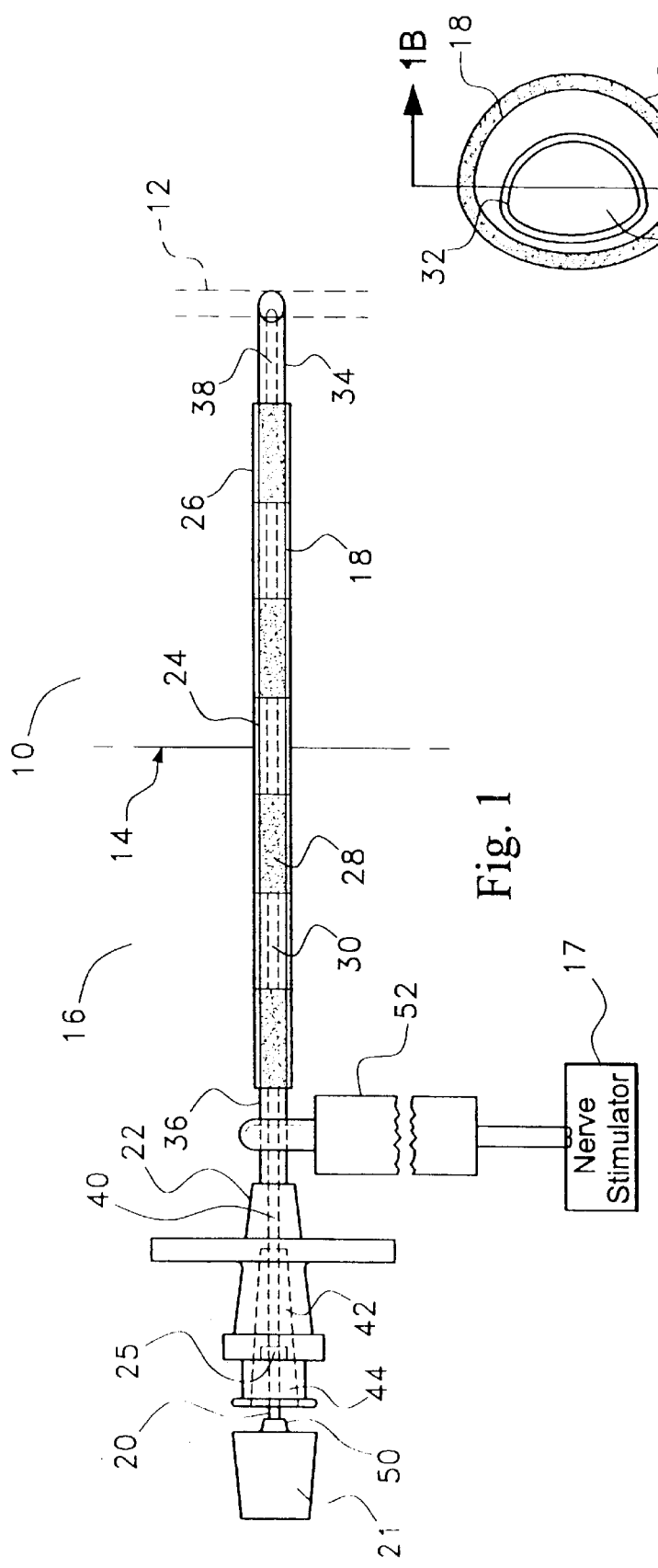
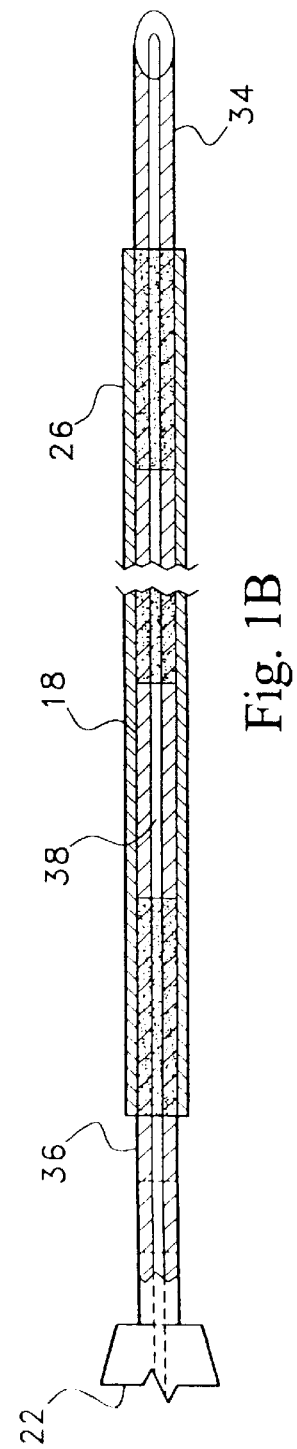
Fig. 1
Fig. 1A
Fig. 1B

INSTRUMENT FOR DELIVERY OF ANAESTHETIC DRUG

BACKGROUND OF THE INVENTION

This invention relates to medical-surgical instruments and a method of utilizing medical-surgical instruments for delivery of an anaesthetic drug. The invention is more particularly concerned with instruments and methods for use in the delivery of an anaesthetic for use as a nerve block.

A nerve block may be achieved through the administration of variable quantities of an anaesthetic agent to the plexus of a nerve. Since the nerve plexus is a very fragile structure, not capable of simple repair or reconstruction, it is crucial to do as little damage as possible in locating the point at which the plexus may be contacted.

It has been proposed to use a needle to locate the nerve in the usual way, and then to insert anaesthetic through the needle so that it emerges from the tip of the needle and contacts the nerve. An alternative procedure involves the proper positioning of the needle and the introduction of an epidural catheter through the needle. Once properly placed adjacent the nerve and into the plexus sheath of the patient, the epidural catheter may then be used to deliver variable amounts of anaesthetic for use as a nerve block.

It has also been proposed that an integral conductive wire be contained in the catheter, through which an electrical current may be applied to determine correct positioning of the catheter once it has been inserted through the needle. An electrical impulse sent through the conductive wire is utilized in determining proper placement of the tip of the catheter and, thus, the point at which the anaesthetic will be delivered.

Certain disadvantages exist with regard to the above referenced methods and the apparatus available to accomplish such methods. Most important among these is a danger associated with the uncertainty regarding the position of the needle tip. Such uncertainty could lead to nerve damage in manipulating the tip of the needle without knowing its position relative to nerves in the patient's body. One reason for this uncertainty can be related to leakage of electricity. Placement of the catheter can have similar difficulties. In addition, the integral conductive wire in the catheter can be difficult to utilize effectively, as it is not rigidly attached to the remainder of the catheter apparatus. The catheter itself can also be unwieldy as it is usually of a very small diameter.

BRIEF SUMMARY OF THE INVENTION

In accordance with the present invention, a catheter system is provided comprising: (a) a needle; (b) a catheter provided with an electrically conductive wire; and (c) a multipurpose connector provided with a structure able to make electrical contact with the conductive wire contained in the catheter.

The needle has a distal end and a proximal end. The distal end of the needle terminates in a beveled aperture having a sharp tip adapted for insertion into a nerve sheath of a patient so as to abut the nerve plexus. Contained in the needle and co-terminus therewith at the distal end is a removable stylet utilized in easing insertion of the needle into the patient. The proximal end of the needle is provided with a hub portion used for gripping the needle as well as for accessing the central bore of the needle. The needle, being of metal construction, is electrically conductive along its entire length. A non-conductive material may be used to coat the outer surface of the needle, leaving exposed portions of the proximal and distal ends of the needle, such that electrical voltage is not expended in unnecessary places.

The catheter is adapted for insertion through the hub portion and within and through the needle, with the distal end of the catheter capable of protruding out of the needle's distal end. The catheter is formed primarily of a thermoplastic or related material which covers a tightly wound helical wire. The helical wire extends beyond the sheath material of the catheter at both the proximal and distal ends thereof. The helix formed by the wire leaves the center of the catheter structure available as a conduit. This central conduit of the catheter allows for administration of anaesthetic to the proximal end of the catheter.

The multipurpose connector allows the proximal end of the catheter to be inserted therein. Once inserted therein, the multipurpose connector may be manipulated to rigidly capture the proximal end of the catheter. The structure of the multipurpose connector allows the proximal end of the catheter to be accessed by a syringe or other apparatus for injecting fluid through the catheter. The multipurpose connector is also provided with electrical connections which electrically contact the helical wire of the catheter. These electrical contacts allow the helical wire of the catheter to be accessed despite the presence of the multipurpose connector over the distal end of the catheter and, thus, the protruding proximal end of the helical wire.

It is therefore an object of the present invention to provide a needle and catheter system including components, such that the position of an epidural needle may be identified by electrically stimulating and thus locating a specific nerve. When a specific nerve is located, the catheter is inserted through the needle to a point slightly beyond the distal tip of the needle. The catheter tip may then be manipulated and the optimum position for the catheter tip determined by applying an electrical voltage through the helical wire to the proximal tip of the helical wire, this electrical stimulation being utilized in locating the specific location of the catheter tip within the nerve. Once optimum placement is achieved, the catheter is utilized for continuous administration of anaesthetic.

Some of the objects of the invention having been stated above, other objects will become evident as the description proceeds below, when taken in connection with the accompanying drawings as best described below.

BRIEF DESCRIPTION OF THE DRAWINGS

FIG. 1 is a side elevational view of the needle and stylet, with the needle inserted into the nerve sheath;

FIG. 1A is an end-on elevational view from the distal end of the needle structure, showing a detail of the tip of the needle, the tip of the stylet the and non-conductive needle material covering the region of the needle between the proximal ends;

FIG. 1B is a side elevational view of the needle, with only a portion of the hub shown and the stylet removed, most of the needle being shown in section at section line 1B—1B;

DETAILED DESCRIPTION OF THE INVENTION

Figure 1D:
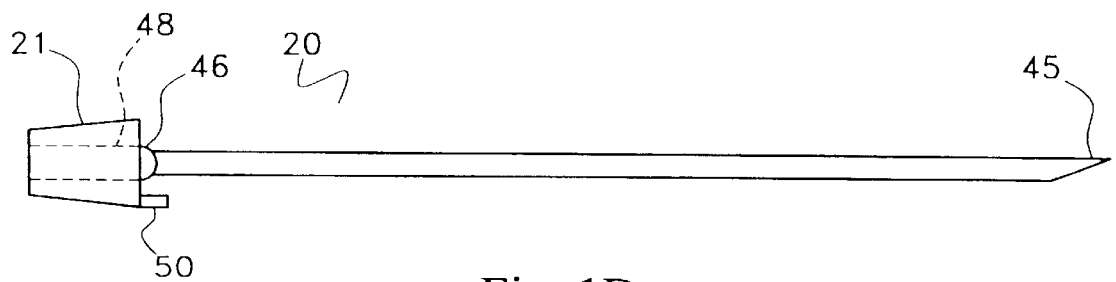
FIG. 1D is a side elevational view of the inner stylet.

Referring first to FIG. 1, there is shown relevant portions of a human body 10 containing a nerve 12 located subcutaneous to adjacent neck portion 14. In this example of use, a needle assembly 16 has been inserted into a specific point in the neck 14 of the human body 10 for the purpose of locating the nerve 12. The needle assembly 16 comprises a needle 18 and a central stylet 20 which extend coaxially of one another. The needle 18 is a metal needle which is joined at its rear end to a hub 22 of a plastic material. The needle 18 is hollow and projects about 95 mm forwardly of the hub 22.

The needle 18 has three portions along its length. The major portion of the needle is the central portion 24 thereof. This central portion 24 of the needle is wrapped on the outside surface thereof in an insulating coating 26 which will not conduct electricity. This coating 26 is shown in FIG. 1 as being divided into sections of alternating color 28 and 30. Each of these sections is of a known, specific, length. Such colored sectioning enables the user to determine the extent of penetration of the tip 32 of the needle 18.

The remaining two portions of the needle 18 are the distal end 34 and the proximal end 36. At its proximal end 36, the needle 18 extends within the hub 22 where it is secured, such as by molding the hub around the needle. Between the insulating coating 26 of the central portion of the needle 24 and the plastic hub 22 the proximal end 36 of the needle 18 is exposed such that electrical contact with the remainder of the needle may be achieved by contact with the exposed proximal end 36. The bore through the needle 38 opens into an axially-aligned bore 40 through the hub 22 of the same diameter as the needle bore 38. The rear end of the bore 42 is enlarged and tapered to provide a female Luer opening 44 for use in receiving the stylet 20 and stylet hub 21. The hub 22 is provided with an axially-extending slot or keyway 25 formed in the outer surface of the hub, on that side of the hub to which the tip 32 of the needle 18 is inclined.

Figure 1C:
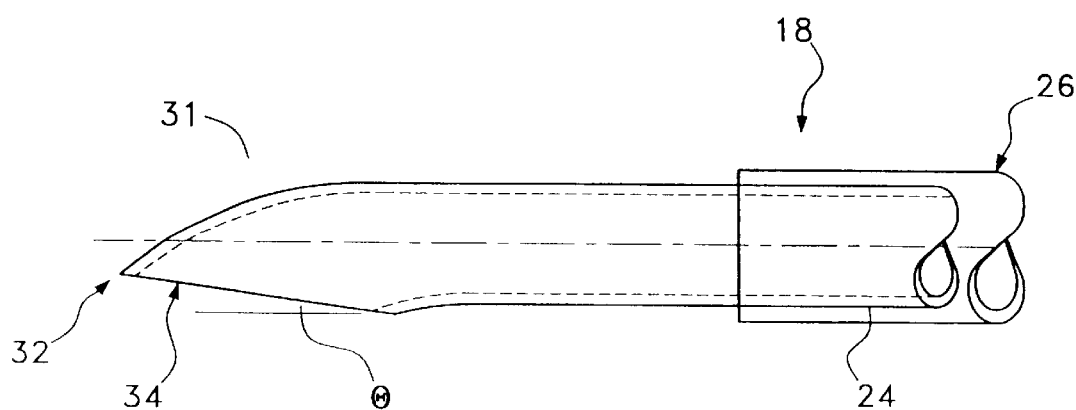
FIG. 1C is a detail of the needle tip.

As shown in FIG. 1C, the forward 5 mm or so 31 of the needle 18 is bent downwardly at an angle of about 20°, the distal end 34 of the needle being cut such that it makes an angle θ of about 10° with the axis of the major part of the needle. This inclined end of the needle provides it with a tip 32 constituting a sharp point that readily pierces body tissue. The distal end 34 of the needle is not covered by any electrically insulating material and is in electrical contact, by way of the covered central portion 24, with the proximal end 36 of the needle. The insulating coating 26 prevents the flow of electricity radially out of the central portion 24 of the needle, but allows the flow of electricity axially along the length of the needle 18.

As best exemplified in FIG. 1D, the inner stylet 20 is formed of a solid metal needle. The distal tip 45 of the stylet 20 is cut to have the same sharp tip angle θ as the tip 32 of the needle. Joined to the proximal end of the stylet 20 is a stylet hub 21 of plastic material. The stylet 20 is smaller in diameter than the outer needle 18 and is straight along its entire length. The connector 46 of the stylet hub 21 which grasps the stylet 20 is of generally cylindrical shape. The forward end of the connector 46 has a Luer taper 48 that is dimensioned to fit within the Luer-tapered opening 44 in the needle hub 22. A short peg or key 50 of rectangular section is provided along the lower side of the stylet hub 21, as viewed in FIG. 1. The peg 50 extends axially of the stylet hub 21, being spaced outwardly by a small gap from its Luer-tapered section 48. The peg 50 is aligned with respect to the stylet hub 21 and stylet 20 such that, when the peg is engaged in the slot 25 of the needle hub 22, the plane of the inclined tip 45 of the stylet 20 lies in the same plane as the inclined tip 34 of the needle. The combined sharp tips of the needle and stylet readily pierces body tissue while the stylet, occupying the center bore 38 of the needle, prevents any tissue from entering the needle bore 38.

Also shown in FIG. 1 is an electrical connector 52, which may be in the form of an alligator clip which conveys electrical impulses from an anaesthetic nerve stimulator 17 to the proximal end of the needle 36.

FIG. 1A is an end on view of the tip of the needle assembly 16, showing the inclined tip of the needle 32 the inclined tip 45 of the stylet 20. Also shown is the insulating coating 26. FIG. 1B is a detail of the needle 18 of the needle assembly, with the stylet 20 removed and only showing a small portion of the hub 22. In addition, the needle 18 of FIG. 1 has been sectioned along section line 1B of FIG. 1A. FIG. 1B shows the relationship of the insulating coating 26 (of exaggerated thickness) to the various portions of the needle 18.

Figure 2:
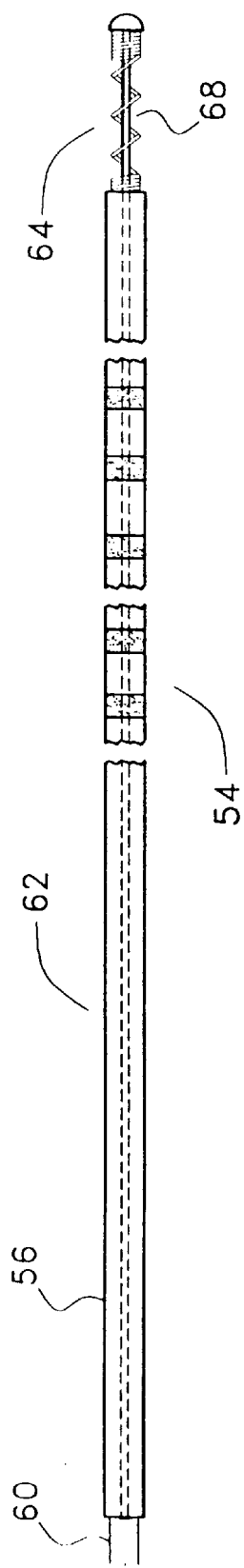
FIG. 2 is a side elevational view of the catheter.
Figure 3:
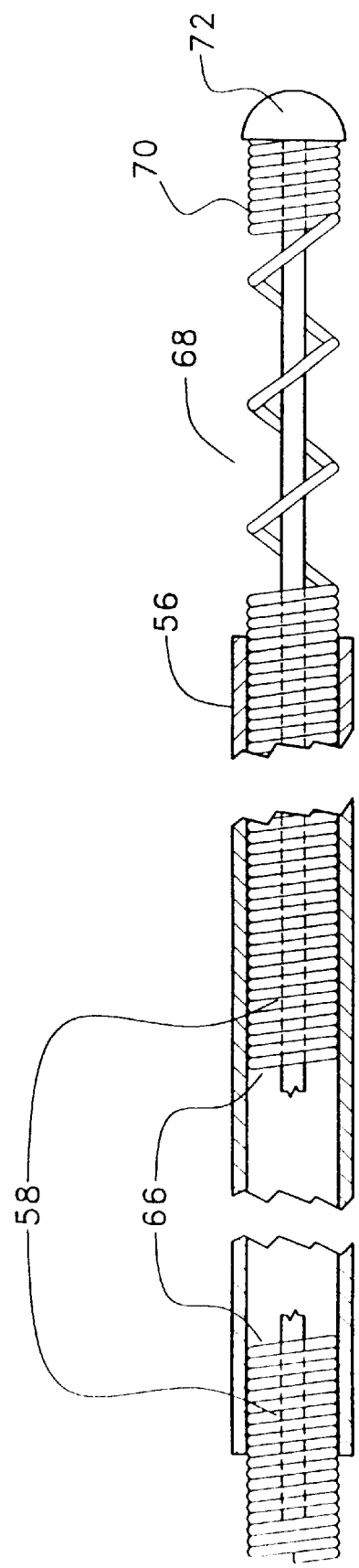
FIG. 3 is an enlarged version of FIG. 2, except that the catheter sheath is partially cut away to better show the structure of the helical wire, only portions of which are shown.

Referring next to FIG. 2, there is shown a catheter assembly 54. The catheter assembly 54 is of a diameter which allows the assembly to be inserted through the needle assembly 16 and into the body of the patient. The catheter assembly 54 comprising a sheath 56 formed from a thermoplastic or similar material. A helical coil of wire 58, best shown in FIG. 3, possesses three portions. A proximal portion 60, a central portion 62 and a distal portion 64. For its entire length, the helical wire 58 defines a central bore 66 through which a liquid may freely pass.

The central portion 60 of the helical wire 58 is completely covered by the catheter sheath 56 and constitutes the vast majority of the total length of the catheter assembly 54. The proximal portion 60 of the helical wire has no distinguishing features except that it is short relative to the central portion of the remainder of the catheter assembly 54 and is not covered by the catheter sheath. The proximal portion of helical wire is left exposed so that it, and therefore the entire wire helix 58, may be electrically contacted, as will be discussed relative to other structures.

The distal portion 64 of the helical wire, which is also short relative to the remainder of the catheter assembly 54 and not covered by the catheter sheath 56, has several features associated therewith. Where the helical wire 58 exits the catheter sheath 56 at the distal end thereof, the helix maintains the tightly wound nature of the proximal 60 and central 62 portions of the wire. This tight helix continues for a short distance along the distal portion before the helix opens up considerably at an open helix portion 68. The open helix portion 68 continues for several revolutions of the helix, before the structure returns for the tightly wound end 70 of the distal portion 64. Attached to the distal end of the tightly wound end portion is a wire helix tip 72 which is a piece of rounded metal.

Figure 4:
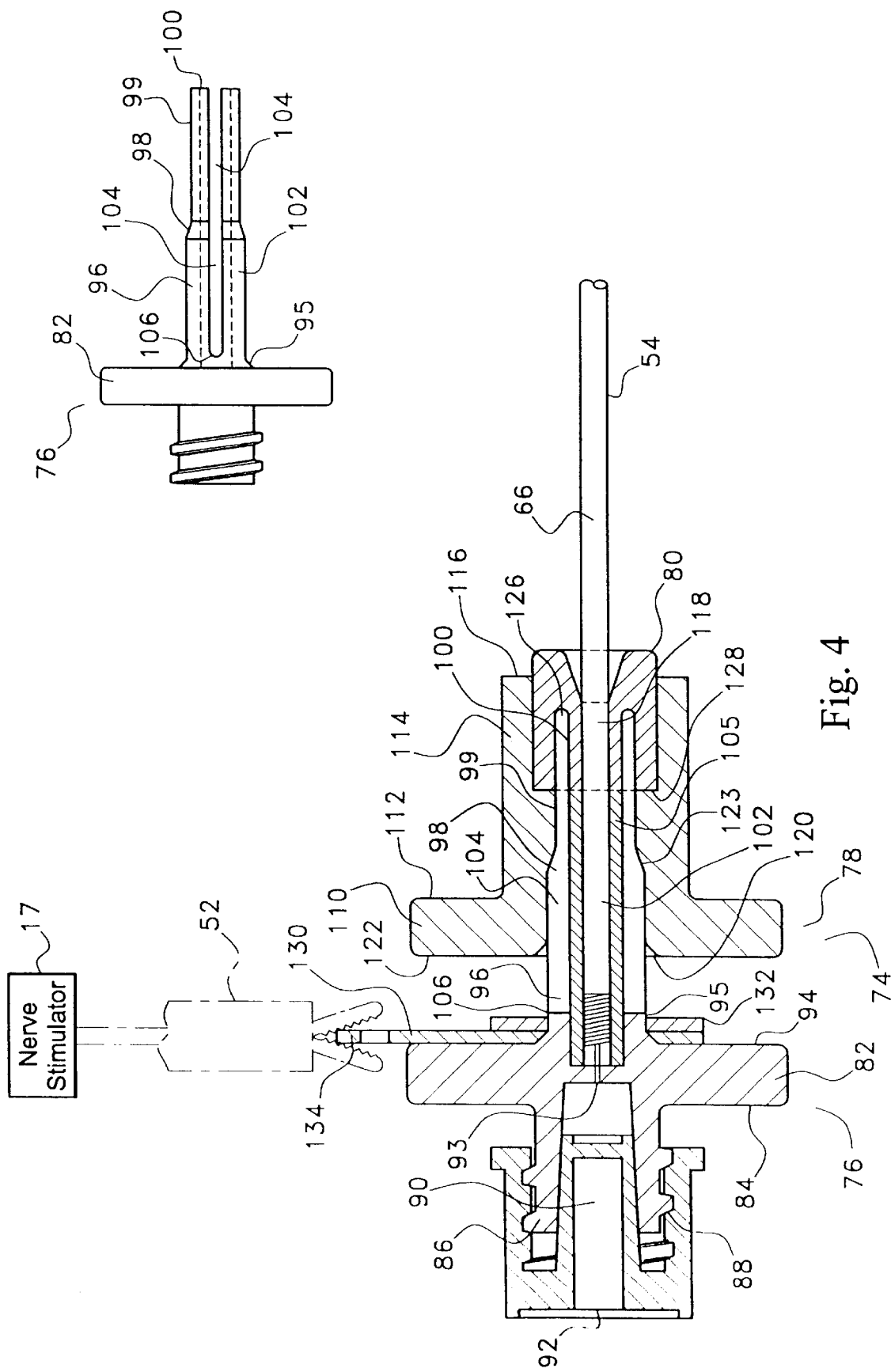
FIG. 4 is a side elevational view of the multipurpose connector in section, with the proximal end of the catheter inserted therein but not yet rigidly held in place.

Referring next to FIG. 4, there is shown a catheter adapter 74. Accessing the central bore 66 of the catheter assembly 54 would be nearly impossible given the diameter of this structure. This being the case, a catheter adapter 74 is needed to provide access to the central bore 66 of the catheter assembly 54 for various delivery vehicles, e.g. a syringe, for the controlled delivery of fluid through the catheter.

The main constituents of the catheter adapter are the rear body 76, the front body 78 and the holding hub 80. The rear body 78 has a central flange 82. From the rear face 84 of the central flange 82 extends a connection cylinder 86 having a threaded outer surface 88 and a hollow central bore 90. The function of this cylinder is to facilitate luer attachment of apparatus for controlled delivery of fluid to the catheter assembly 54. The end cap 92 provided with the catheter adapter 74 is primarily for sterility purposes, and is simply removed after the catheter adapter 74 is attached to the catheter assembly 54. The central flange has, at its center, a bore 93 passing completely therethrough such that the rear face 84 and front face 94 are in fluid communication.

From the front face 94 of the central flange 82 extends an operating cylinder 96. Where the operating cylinder 96 is connected to the front face 94 of the central flange 82, it is of a certain diameter 95. Along the length of the operating cylinder, the diameter of the operating cylinder is reduced by a taper 98. The remainder of the operating cylinder is of this reduced diameter 99 to the distal end 100 of the operating cylinder. The operating cylinder 96 has a central bore 102 which extends along the entire length thereof. Axial slots 104 extend from the distal end 100 of the operating cylinder, nearly the length thereof, i.e. the slot ends 106 extend nearly to the juncture of the operating cylinder 96 and the front face 94 of the central flange 82. Contained in and extending most of the length of the central bore 102 of the operating cylinder 96 is an elongated rubber gasket 105.

The front body 78 of the catheter adapter has a structure similar in geometry to the central flange 82 the rear body 76, this structure is called the rear flange 110. The rear flange 110 has extending from the front face 112 thereof a front cylinder 114. The front cylinder 114 has an essentially constant outside diameter extending from the front face 112 of the rear flange 110 to the distal end 116 of the front cylinder. A central bore 118 is provided in the front cylinder 114, extending the entire length thereof. This central bore 118 has several different diameter changes along its length. At the entry portion of the central bore 120 on the rear face 122 of the rear flange, the diameter of the bore is slightly larger that the diameter 95 of the operating cylinder 96 where it is connected to the front face 94 of the central flange 82. Along the length of the central bore 120 the inside diameter is reduced by a taper 123 which is a mirror image of taper 98 on the operating cylinder. These mirror image structures thus allow sliding contact between the outer surface of the operating cylinder 96 and the central bore 120 of the front body 78.

The holding hub 80 is a generally tubular body provided with a cylindrical recess 126 formed in the rear face 128 thereof. The distal end 100 of the operating cylinder 96 is matingly engageable with the cylindrical recess 126 of the holding hub 80 and is rigidly attached thereto. The diameter of the central bore 120 of the front body 78 is, from the front face thereof 94 to a depth less than the length of the holding hub, slightly greater than the diameter of the holding hub. The rigid connection between the holding hub 80 and the distal end 100 of the operating cylinder holds these two structures in slidable relationship with the front body 78.

In use, the catheter adapter 74 is initially in the configuration shown in FIG. 4. In this configuration the proximal end 57 of the catheter assembly 54 may be freely inserted and withdrawn from the catheter adapter. The proximal end 57 of the catheter assembly 54 may be held in place by sliding the front body 78 toward the rear body 76 of the catheter adapter. In sliding these pieces relative to each other, the taper 98 of the operating cylinder 96 will be compressed by the taper 123 of the interior of the front body. The slots 104 in the operating cylinder 96 allow this compression to occur. The compression of the operating cylinder results in the compression of the elongated rubber gasket 105. This compression of the elongated rubber gasket 105 results in the rubber gasket fictionally engaging the proximal end 57 of the catheter assembly 54 such that the catheter may not be easily removed from the catheter adapter.

Figure 6:
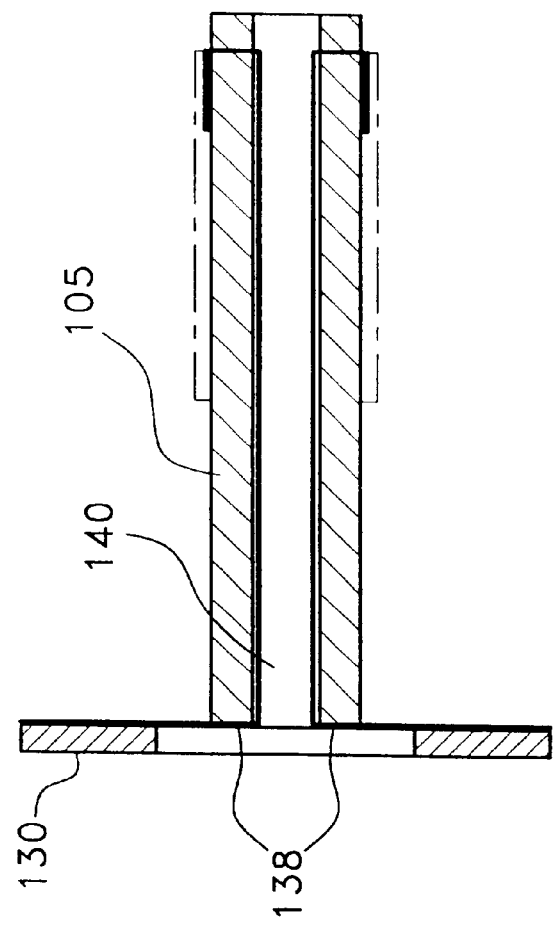
FIG. 6 is a side elevational view of the metal washer, multipurpose connector wires and sealing assembly of the multipurpose connector.
Figure 5:
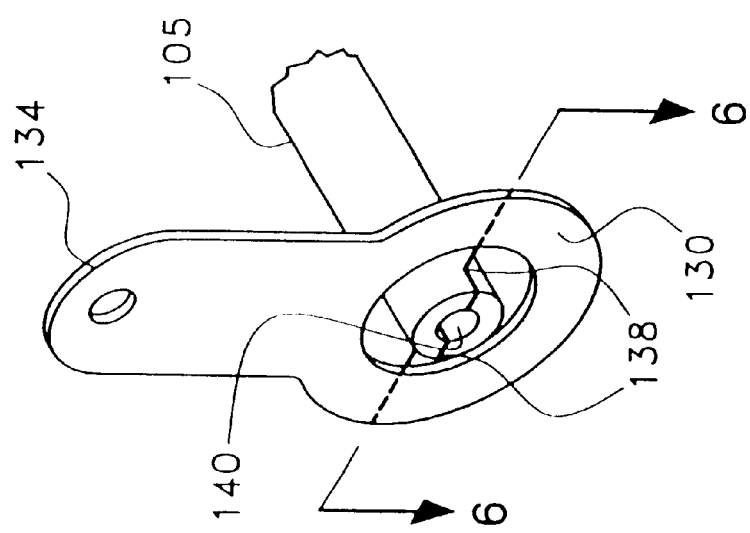
FIG. 5 is a perspective view of the metal washer, multipurpose connector wires and sealing assembly of the multipurpose connector.

An additional structure of the catheter adapter which is of interest is the metal washer 130. This metal washer 130 is disposed about the operating cylinder 96 adjacent the front face 94 of the central flange 82, and is held in place by nut 132. The metal washer 130 is provided with a tab portion 134 which extends above the flange portions 82 and 110. This allows electrical contact to be made to the washer by way of the same electrical connector 52 as was used previously to conduct electricity into the needle assembly 16 from an anaesthetic nerve stimulator 17. As can be seen in FIGS. 5 and 6, a pair of wires 138 are attached to the metal washer 130 and extend from the metal washer to the internal bore 140 of the elongated rubber gasket 105. Thus, when the elongated rubber gasket 105 is compressed about the proximal end of the catheter assembly 54 and about the exposed helical wire 58 found at the proximal portion 60 thereof, electrical contact is made between the pair of wires 138 and the helical wire 58. As a result, electrical contact may be made from the anaesthetic nerve stimulator 17, through the catheter adapter 74 and into the helical wire 58 of the catheter apparatus 54 and, thus, to the distal wire helix tip 72 of the catheter assembly.

The above described apparatus may be used in numerous different medical procedures. The following described medical procedure is one type which utilizes the features embodied in the above described apparatus. The method is drawn to the correct placement of the catheter assembly 54 and, more particularly, the distal portion 64 thereof. Once the distal portion 64 of the catheter assembly 54 is determined to be in the correct position, a continuous interscalene nerve block may be administered.

The patient is positioned in the dorsal recumbent position with the head slightly in extension and turned somewhat to the opposite side. An assistant applies light traction on the arm with the elbow flexed.

The interscalene groove is easily palpated in this position by the following procedure: First, the posterior edge of the clavicular head of the sternocleidomastoid muscle is located; then the palpating fingers are placed postero-lateral to this muscle to identify the interscalene groove. The external jugular vein almost always lies directly superficial to the interscalene groove and provides a useful additional landmark. Needle entry should be anterior or posterior to the vein. Another constant finding is that the interscalene groove is approximately 3 cm lateral to the most prominent portion of the belly of the sternocleidomastoid muscle at the level of the cricoid cartilage.

The needle assembly 16 is inserted into the interscalene groove at the level of the cricoid (C6 level) and the needle is directed perpendicular to the skin in all the planes. For the placement of the catheter assembly 54 for this continuous interscalene nerve block technique, the needle assembly 16 enters the skin at a point approximately halfway between the mastoid and the clavicle, posterior to the posterior border of the clavicular head of the sternocleidomastoid muscle.

The point of needle entry is just caudal to the accessory nerve and just posterior to the anterior border of the posterior triangle of the neck. The accessory nerve can usually be identified by stimulating percutaneously with the electrical connector 52 of the nerve stimulator 17 since the nerve runs superficial to the fascial carpet of the posterior triangle of the neck, approximately midway between the clavicle and the mastoid. When the needle tip 32 is proximate the accessory nerve and voltage from the nerve stimulator 17 is applied, contractions of the trapezius muscle and elevation of the shoulder girdle will occur. The needle assembly 16 is directed caudal and parallel to the vertebrae aiming for the interscalene groove with the bevel of the needle assembly 16 directed laterally (outwards) to avoid possible central (epidural) placement of the catheter.

During insertion of the needle assembly, voltage should be continuously applied to the needle tip 32 as an aid in navigating the various nerves which may be encountered. The nerves to the levator scapula and rhomboid muscles may be encountered with the needle 32 tip at an early point. Stimulation of these nerves will also cause movement of the shoulder girdle when stimulated by elevating or rotating the scapula. The phrenic nerve, situated on the belly of the anterior scalene muscle, may be encountered. This causes unmistakable twitching of the ipsilateral diaphragm. All these nerves should be avoided by redirection and/or reinsertion of the needle assembly 16 as stimulation of these nerves can provide false indications of correct needle placement that will most certainly lead to block failure or phrenic nerve paralysis if local anesthetic agent is injected at this stage.

When the brachial plexus is encountered, definite and unmistakable muscle twitchings should be observed in the biceps and deltoid muscles of which the biceps movements are more easily seen. This is the reason for keeping the elbow slightly flexed during the procedure. If the phrenic nerve is accidentally stimulated the needle assembly 16 is pulled back slightly and the needle tip 32 is directed slightly posteriorly until the brachial plexus is encountered. As the needle tip 32 is advanced further a distinct "pop" or give can be felt followed by an increased intensity of the biceps and deltoid muscle twitchings. This is when the fascia sheath of the brachial plexus is penetrated and the tip of the needle 32 is now in direct contact with the brachial plexus. The electrical connector 52 may be removed from the needle 18 at this time.

The central stylet 20 is removed from the needle 18 and the catheter assembly 54 is fed through the needle 18 to a point just past the tip of the needle 32. Such a placement of the wire helix tip 72 is far enough so that the metal helical wire 58 does not make contact with the needle, i.e. the needle tip 32 is in contact with the catheter sheath 56 which will not conduct (disperse) electricity.

The catheter adapter 74 can be attached to the proximal end 60 of the catheter assembly 54 at this point, if it has not been attached previously. The electrical connector 52 of the nerve stimulator 17 is then clipped to the tab portion 134 of the metal washer 130 provided on the catheter adapter 74.

The output of the nerve stimulator 17 can be turned down (typically to approximately 0.5–1.0 mA) as the muscle twitching will increase because all the current is now concentrated in the unsheathed helix tip 72 of the catheter assembly 54. Muscle contractions with a nerve stimulator 17 output of approximately 0.5 mA provides additional proof of proper placement into the sheath.

Advancement of the catheter helical tip 72 approximately an additional 1 cm beyond the tip of the needle 32 down the brachial plexus sheath should not result in a decreasing of the twitching in the biceps and deltoid muscles. Frequently, though, the muscle twitchings do decrease in which case the needle and catheter complex 16, 54 are simultaneously pulled back slightly as a unit, until maximal twitchings are again observed. The catheter 54 is then again advanced and the above process is repeated until maximal twitchings are observed during catheter 54 advancement. It is most important for guaranteed successful catheter placement to observe maximal muscle contractions while catheter is being advanced. The catheter 54 frequently cannot be fed beyond the coracoid process. It should, however, not be forced further as this may lead to nerve damage and, for shoulder surgery, it is not necessary to advance the catheter beyond this point. The needle assembly 16 may then removed and the catheter securely fixed.

Indwelling interscalene catheters are notorious for falling out or dislodging. To avoid dislodgment after placement of the catheter, the same needle 16 used to place the catheter, is inserted subcutaneously from just above the suprasternal notch and directed superolaterally, avoiding vascular structures, towards the point of entry of the catheter. The needle assembly 16 is advanced to exit through the same orifice in the skin as the catheter 54 and just next to the catheter. The proximal end of the catheter 60 is fed from the tip of the needle 32 through the needle 18 and the needle is removed so that the catheter 54 is tunneled subcutaneously.

Kinking of the catheter should be avoided as the elbow formed by the catheter disappears under the skin. The catheter is then covered with a transparent dressing.

With the catheter assembly thus firmly in place, anaesthetic may be administered to effectuate a nerve block:

1. When a dense motor and sensory block is required:
    a) Ropivacaine 10 mg/mL (1%). Inject 20 mL as a bolus and then infuse with syringe driver a diluted concentration (5 mg/mL or 0.5%) at 10–20 mL/hour.
    Or
    b) Bupivacaine 5 mg/mL (0.5%). Inject 20 mL as a bolus and then infuse a diluted concentration (2.5 mg/mL or 0.25%) at 10–20 mL/hour.
2. When sensory block with minimal motor block is required:
    a) Ropivacaine 2 mg/mL (0.2%). Inject 10–20 mL as a bolus and then infuse the same concentration at 1–10 mL/hour. Continually adjust (titrate) the infusion rate to achieve the desired effect.
    Or
    b) Bupivacaine 2.5 mg/mL (0.25%). Inject 10–20 mL as a bolus and the infuse the same concentration at 1–10 mL/hour. Continually adjust (titrate) the infusion rate to achieve the desired effect.
3. Patient Controlled Interscalene Nerve Block:
    Injection if a bolus of 30 mL bupivacaine (0.4%) via an indwelling catheter into the brachial plexus sheath at the level of the interscalene groove followed by a background infusion of bupivacaine 0.15% at a rate of 5 mL/hour and a patient-controlled bolus of 4 mL for patients weighing>65 Kg and 3 mL for patients weighing<65 Kg. A lockout time of 20 minutes was programmed into the PCA device. This seemed successful. Promising preliminary results have been achieved with ropivacaine. It seems that finer adjustment of the block to achieve varying levels and densities of motor and sensory blockade may be possible with ropivacaine.

While the foregoing invention has been described in some detail for purposes of clarity and understanding, it will be appreciated by one skilled in the art, from a reading of the disclosure, that various changes in form and detail can be made without departing from the true scope of the invention in the appended claims.

What is claimed is:

1. A medical-surgical instrument comprising:
   a. a needle comprising an central bore and an outer surface, the needle capable of conveying an electrical impulse from a proximal end to a distal tip of the needle, a portion of the outer surface of the needle between the proximal end and distal tip is wrapped in an electrically insulating coating;
   b. means for connecting an electrical impulse to the proximal end of the needle;
   c. a catheter covering a helical wire, a distal end of the helical wire terminating at a helix tip extends distally beyond a distal end of the catheter, a proximal end of the helical wire extends proximally beyond a proximal end of the catheter, the helical wire capable of conveying a second electrical impulse from the proximal end of the helical wire to the helix tip, the catheter being inserted through the central bore such that the helix tip extends beyond the distal tip of the needle;
   d. means for facilitating attachment of an apparatus for the controlled delivery of fluid to the proximal end of the catheter assembly;
   e. means for conveying the second electrical impulse through the apparatus for controlled delivery of fluid to the proximal end of the helical wire.

* * * * *